(12) United States Patent
Kaplan et al.

(10) Patent No.: US 9,599,891 B2
(45) Date of Patent: Mar. 21, 2017

(54) FABRICATION OF SILK FIBROIN PHOTONIC STRUCTURES BY NANOCONTACT IMPRINTING

(75) Inventors: David L. Kaplan, Concord, MA (US); Fiorenzo G. Omenetto, Lexington, MA (US); Luca Dal Negro, Cambridge, MA (US)

(73) Assignees: TRUSTEES OF TUFTS COLLEGE, Medford, MA (US); TRUSTEES OF BOSTON UNIVERSITY, Boston, MA (US)

( * ) Notice: Subject to any disclaimer, the term of this patent is extended or adjusted under 35 U.S.C. 154(b) by 1184 days.

(21) Appl. No.: 12/741,066

(22) PCT Filed: Nov. 5, 2008

(86) PCT No.: PCT/US2008/082487
§ 371 (c)(1),
(2), (4) Date: Jan. 30, 2012

(87) PCT Pub. No.: WO2009/061823
PCT Pub. Date: May 14, 2009

(65) Prior Publication Data
US 2012/0121820 A1    May 17, 2012

Related U.S. Application Data

(60) Provisional application No. 60/985,310, filed on Nov. 5, 2007.

(51) Int. Cl.
*G03F 7/00* (2006.01)
*B29D 11/00* (2006.01)
(Continued)

(52) U.S. Cl.
CPC ............ *G03F 7/0002* (2013.01); *B29D 11/00* (2013.01); *B29D 11/00346* (2013.01);
(Continued)

(58) Field of Classification Search
CPC ......... B82Y 10/00; G02B 6/1225; G02B 1/04
(Continued)

(56) References Cited

U.S. PATENT DOCUMENTS 4,180,604 A * 12/1979 Feng et al. .................... 430/168
4,676,640 A    6/1987 Briggs
(Continued)

FOREIGN PATENT DOCUMENTS

EP    0245509 A1    11/1987
EP    1116987 A2    7/2001
(Continued)

OTHER PUBLICATIONS

Dauksher et al. "Characterization of and imprint results using indium tin oxide based step and flash imprint lithography temp ates" Journal of Vacuum Science Technology B vol. 20 Iss 6. 2002.*
(Continued)

*Primary Examiner* — Dah-Wei D Yuan
*Assistant Examiner* — Jose Hernandez-Diaz
(74) *Attorney, Agent, or Firm* — Choate, Hall & Stewart, LLP

(57) ABSTRACT

A method of manufacturing a nanopatterned biophotonic structure includes forming a customized nanopattern mask on a substrate using E-beam lithography, providing a biopolymer matrix solution, depositing the biopolymer matrix solution on the substrate, and drying the biopolymer matrix solution to form a solidified biopolymer film. A surface of the film is formed with the nanopattern mask, or a nanopattern is machined directly on a surface of the film using E-beam lithograpy such that the biopolymer film exhibits a spectral signature corresponding to the E-beam lithograpy nanopattern. The resulting bio-compatible nanopatterned biophotonic structures may be made from silk, may be biodegradable, and may be bio-sensing devices. The bio-
(Continued)

photonic structures may employ nanopatterned masks based on non-periodic photonic lattices, and the biophotonic structures may be designed with specific spectral signatures for use in probing biological substances, including displaying optical activity in the form of opalescence.

19 Claims, 9 Drawing Sheets

(51) Int. Cl.
  G02B 6/122    (2006.01)
  C07K 14/435   (2006.01)
  B82Y 10/00    (2011.01)
  B82Y 20/00    (2011.01)
  B82Y 40/00    (2011.01)
(52) U.S. Cl.
  CPC ............... B82Y 10/00 (2013.01); B82Y 20/00 (2013.01); B82Y 40/00 (2013.01); C07K 14/435 (2013.01); G02B 6/1225 (2013.01)
(58) Field of Classification Search
  USPC .................................. 427/552, 53, 555, 556
  See application file for complete search history.

(56) References Cited

U.S. PATENT DOCUMENTS

| | | |
|---|---|---|
| 5,252,285 A | 10/1993 | Lock |
| 5,427,096 A | 6/1995 | Bogusiewicz et al. |
| 5,512,218 A | 4/1996 | Gresser et al. |
| 6,134,045 A | 10/2000 | Jiang et al. |
| 6,150,491 A | 11/2000 | Akkara |
| 6,284,418 B1 | 9/2001 | Trantolo |
| 6,423,252 B1* | 7/2002 | Chun et al. .................. 264/28 |
| 6,671,034 B1* | 12/2003 | Hatakeyama et al. ........ 355/67 |
| 6,924,503 B2 | 8/2005 | Cheng et al. |
| 6,989,897 B2 | 1/2006 | Chan et al. |
| 6,992,325 B2 | 1/2006 | Huang |
| 7,223,609 B2 | 5/2007 | Anvar et al. |
| 8,005,526 B2 | 8/2011 | Martin et al. |
| 2001/0002417 A1 | 5/2001 | Akkara et al. |
| 2001/0003043 A1 | 6/2001 | Metspalu et al. |
| 2003/0017581 A1* | 1/2003 | Li .................. G01N 21/7743  435/287.2 |
| 2003/0203366 A1 | 10/2003 | Lim et al. |
| 2003/0214057 A1 | 11/2003 | Huang |
| 2003/0219992 A1* | 11/2003 | Schaper ................ 438/748 |
| 2004/0001299 A1 | 1/2004 | van Haaster et al. |
| 2004/0029241 A1 | 2/2004 | Hahn et al. |
| 2004/0081384 A1 | 4/2004 | Datesman et al. |
| 2004/0229349 A1 | 11/2004 | Daridon |
| 2005/0008675 A1 | 1/2005 | Bhatia et al. |
| 2005/0151966 A1 | 7/2005 | Packirisamy et al. |
| 2005/0194365 A1 | 9/2005 | Li |
| 2005/0213868 A1 | 9/2005 | Cunningham |
| 2005/0217990 A1 | 10/2005 | Sibbett et al. |
| 2005/0276791 A1 | 12/2005 | Hansford et al. |
| 2006/0042822 A1 | 3/2006 | Azeyanagi et al. |
| 2006/0091571 A1 | 5/2006 | Akutsu et al. |
| 2006/0134606 A1 | 6/2006 | Montagu |
| 2006/0141617 A1 | 6/2006 | Desai et al. |
| 2006/0177479 A1 | 8/2006 | Giachelli et al. |
| 2006/0178655 A1 | 8/2006 | Santini et al. |
| 2006/0226575 A1 | 10/2006 | Maghribi et al. |
| 2006/0236436 A1* | 10/2006 | Li et al. .................. 977/721 |
| 2006/0286663 A1* | 12/2006 | Cunningham ........ B01L 3/5085  435/287.2 |
| 2007/0007661 A1 | 1/2007 | Burgess et al. |
| 2007/0009968 A1 | 1/2007 | Cunningham et al. |
| 2007/0026064 A1 | 2/2007 | Yoder et al. |
| 2007/0031607 A1 | 2/2007 | Dubson et al. |
| 2007/0042505 A1 | 2/2007 | Israel et al. |
| 2007/0058254 A1 | 3/2007 | Kim |
| 2007/0073130 A1 | 3/2007 | Finch et al. |
| 2007/0178240 A1 | 8/2007 | Yamazaki et al. |
| 2007/0202343 A1* | 8/2007 | Sprenger et al. .............. 428/432 |
| 2007/0233208 A1 | 10/2007 | Kurtz et al. |
| 2008/0019925 A1 | 1/2008 | Begleiter |
| 2008/0038236 A1 | 2/2008 | Gimble et al. |
| 2008/0152281 A1 | 6/2008 | Lundquist et al. |
| 2008/0203431 A1 | 8/2008 | Garcia et al. |
| 2008/0239755 A1 | 10/2008 | Parker et al. |
| 2008/0288037 A1 | 11/2008 | Neysmith et al. |
| 2009/0028910 A1 | 1/2009 | DeSimone et al. |
| 2009/0208555 A1 | 8/2009 | Kuttler et al. |
| 2010/0028451 A1 | 2/2010 | Kaplan et al. |
| 2010/0063404 A1 | 3/2010 | Kaplan et al. |
| 2010/0120116 A1 | 5/2010 | Kaplan et al. |

FOREIGN PATENT DOCUMENTS

| | | |
|---|---|---|
| EP | 1166987 A2 | 1/2002 |
| EP | 1467224 A1 | 10/2004 |
| JP | 60142259 A | 7/1985 |
| JP | 60155129 A | 8/1985 |
| JP | 01280242 A | 11/1989 |
| JP | 02086799 A | 3/1990 |
| JP | 11042106 A | 2/1999 |
| JP | H11-183854 A | 7/1999 |
| JP | 2000096490 A | 4/2000 |
| JP | 2000143472 A | 5/2000 |
| JP | 2000-180969 A | 6/2000 |
| JP | 2001147301 A | 5/2001 |
| JP | 2001280242 A | 10/2001 |
| JP | 2002287377 A | 10/2002 |
| JP | 2003195001 A | 7/2003 |
| JP | 2003322729 A | 11/2003 |
| JP | 2004162209 A | 6/2004 |
| JP | 2004-307661 A | 11/2004 |
| JP | 2005530983 A | 10/2005 |
| JP | 2006241450 A | 9/2006 |
| JP | 2011-504421 A | 2/2011 |
| KR | 20060027113 A | 3/2006 |
| KR | 20070060822 A | 6/2007 |
| KR | 20080069553 A | 7/2008 |
| WO | WO-9315244 A1 | 8/1993 |
| WO | WO-0031752 A2 | 6/2000 |
| WO | WO-0185637 A2 | 11/2001 |
| WO | WO-03038033 A2 | 5/2003 |
| WO | WO-2004000915 A2 | 12/2003 |
| WO | WO-2004092250 A1 | 10/2004 |
| WO | WO-2005012606 A2 | 2/2005 |
| WO | WO-2005019503 A2 | 3/2005 |
| WO | WO-2005/031724 A1 | 4/2005 |
| WO | WO-2005/068980 A1 | 7/2005 |
| WO | WO-2006020507 A1 | 2/2006 |
| WO | 2008/118211 A2 | 10/2008 |
| WO | WO-2008127403 A2 | 10/2008 |
| WO | WO-2008127405 A2 | 10/2008 |
| WO | WO-2009061823 A1 | 5/2009 |
| WO | WO-2010059963 A2 | 5/2010 |

OTHER PUBLICATIONS

Wei et al. "Silicon and polymer nanophotic devices based on photonic crystals" Optoelectronic Integrated Circuits VII (2006). SPIE vol. 6124, 612410 and Sprenger et al. U.S. Pat. No. 2007/0202343.*
Wang et al. "Biomaterial Coatings by Stepwise Deposition of Silk Fibroin". Langmuir 2005, 21, 11335-11341.*
Bai, J. et al., Regenerated spider silk as a new biomaterial for MEMS, Biomed Microdevices, 8:317-323 (2006).
Chrisey, D.B. et al., Laser Deposition of Polymer and Biomaterial Films, Chem. Rev 103(2):553-576 (2003).
Fukuoka T. et al., Enzymatic Polymerization of Tyrosine Derivatives. Peroxidase- and Protease-Catalyzed Synthesis of Poly(tyrosine)s with Different Structures, Biomacromolecules 3(4):768-774 (2002).
International Search Report of PCT/US2007/083600, mailed Nov. 5, 2008, 5 pages.

(56) References Cited

OTHER PUBLICATIONS

International Search Report of PCT/US2007/083605, mailed Dec. 15, 2008, 6 pages.
International Search Report of PCT/US2007/083620, mailed Dec. 5, 2008, 4 pages.
International Search Report of PCT/US2007/083634, mailed Nov. 5, 2008, 5 pages.
International Search Report of PCT/US2007/083639, mailed Dec. 12, 2008, 5 pages.
International Search Report of PCT/US2007/083642, mailed Nov. 5, 2008, 5 pages.
International Search Report of PCT/US2007/083646, mailed Dec. 15, 2008, 6 pages.
International Search Report of PCT/US2008/082487, mailed Feb. 27, 2009, 3 pages.
International Search Report of PCT/US2009/047751, mailed Feb. 2, 2010, 3 pages.
International Search Report of PCT/US2010/022701, mailed Mar. 31, 2010, 2 pages.
International Search Report of PCT/US2010/024004, mailed Nov. 26, 2010, 5 pages.
International Search Report of PCT/US2010/042585, mailed May 25, 2011, 8 pages.
International Search Report of PCT/US2010/047307, mailed Apr. 28, 2011, 3 pages.
International Search Report of PCT/US2010/050468, mailed Jan. 6, 2011, 3 pages.
International Search Report of PCT/US2011/028094, mailed Jul. 14, 2011, 4 pages.
International Search Report of PCT/US2011/032195, mailed Oct. 27, 2011, 3 pages.
International Search Report of PCT/US2011/041002, mailed Feb. 29, 2012, 4 pages.
IPRP of PCT/US2007/083600, mailed May 5, 2009, 6 pages.
IPRP of PCT/US2007/083605, mailed May 5, 2009, 10 pages.
IPRP of PCT/US2007/083620, mailed May 5, 2009, 6 pages.
IPRP of PCT/US2007/083634, mailed May 5, 2009, 6 pages.
IPRP of PCT/US2007/083639, mailed May 5, 2009, 6 pages.
IPRP of PCT/US2007/083642, mailed May 5, 2009, 6 pages.
IPRP of PCT/US2007/083646, mailed May 5, 2009, 10 pages.
IPRP of PCT/US2008/082487, mailed May 11, 2010, 10 pages.
IPRP of PCT/US2009/047751, mailed Dec. 18, 2010, 5 pages.
IPRP of PCT/US2010/022701, mailed Aug. 2, 2011, 5 pages.
IPRP of PCT/US2010/024004, mailed Aug. 16, 2011, 6 pages.
IPRP of PCT/US2010/042585, mailed Jan. 24, 2012, 6 pages.
IPRP of PCT/US2010/047307, mailed Mar. 6, 2012, 5 pages.
Jin, I.J. et al., Water-Stable Silk Films with Reduced Beta-Sheet Content, Adv. Funct. Mater., 15:1241-1247 (2005).
Lawrence, B.D. et al., Bioactive silk protein biomaterial systems for optical devices, Biomacromolecules, 9:1214-1220 (2008).
Min, B.M. et al., Regenerated Silk Fibroin Nanofibers: Water Vapor-Induced Structural Changes and Their Effects on the Behavior of Normal Human Cells, Macromol. Biosci., 6(4):285-292 (2006).
Minoura, N. et al., Attachment and Growth of Cultured Fibroblast Cells on Silk Protein Matrices, J. Biomed. Mater. Res. 29(10):1215-1221 (1995).
Notification of Transmittal of International Search Report and the Written Opinion of PCT/US2011/032195, mailed Oct. 27, 2011, 2 pages.
Ramanujam, P.S., Optical Fabrication of Nano-Structured Biopolymer Surfaces, Opt. Mater. 27:1175-1177 (2005).
Verma, M.K. et al., Embedded Template-Assisted Fabrication of Complex Microchannels in PDMS and Design of a Microfluidic Adhesive, Langmuir, 22(24)10291-10295 (2006).
Written Opinion of PCT/US2007/083600, mailed Nov. 5, 2008, 5 pages.
Written Opinion of PCT/US2007/083605, mailed Dec. 15, 2008, 9 pages.
Written Opinion of PCT/US2007/083620, mailed Dec. 5, 2008, 5 pages.
Written Opinion of PCT/US2007/083634, mailed Nov. 5, 2008, 5 pages.
Written Opinion of PCT/US2007/083639, mailed Dec. 12, 2008, 5 pages.
Written Opinion of PCT/US2007/083642, mailed Nov. 5, 2008, 5 pages.
Written Opinion of PCT/US2007/083646, mailed Dec. 15, 2008, 9 pages.
Written Opinion of PCT/US2008/082487, mailed Feb. 27, 2009, 9 pages.
Written Opinion of PCT/US2009/047751, mailed Feb. 2, 2010, 4 pages.
Written Opinion of PCT/US2010/022701, mailed Mar. 31, 2010, 4 pages.
Written Opinion of PCT/US2010/024004, mailed Nov. 23, 2010, 5 pages.
Written Opinion of PCT/US2010/042585, mailed May 25, 2011, 5 pages.
Written Opinion of PCT/US2010/047307, mailed on Apr. 28, 2011, 4 pages.
Written Opinion of PCT/US2011/032195, mailed Oct. 27, 2011, 5 pages.
Xu, P. and Kaplan, D.L., Horseradish peroxidase catalyzed polymerization of tyrosine derivatives for nanoscale surface patterning, Journal of Macromolecular Science, Part A: Pure and Applied Chemistry, 41(12):1437-1445 (2004).
Yang, L.J. et al., Fabrication of SU-8 embedded microchannels with circular cross-section, International Journal of Machine Tools & Manufacturing, 44:1109-1114 (2004).
Jiang, Wei et al., "Silicon and Polymer Nanophotonic Devices Based on Photonic Crystals" Proc. of SPIE, 6124(1): 612410-1 (2006).
Kouba, J. et al., "Fabrication of Nanoimprint Stamps for Photonic Crystals" Journal of Physics, 34(1): 897-903 (2006).
Tu, D. et al., "A ZEP520-LOR Bilayer Resist Lift-Off Process by E-Beam Lithography for Nanometer Pattern Transfer" Proceedings of the 7th IEEE Conference on Nanotechnology, pp. 624-627, 2007.
Wang, L. et al., "Fabrication of Polymer Photonic Crystal Superprism Structures Using Polydimethylsiloxane Soft Molds" Journal of Applied Physics, 101(11): 114316/1-6 (2007).
Hakimi et al., Spider and mulberry silkworm silks as compatible biomaterials, Composites Part B: Engineering, Elsevier, UK, 38(3): 324-337 (2007).
Kundu et al, Silk fibroin nanoparticles for cellular uptake and control release, Int'l J O Pharmaceutics, 388:242-250 (2010).
Lussi, J.W. et al., Selective molecular assembly patterning at the nanoscale: a novel platform for producing protein patterns by electron-beam lithography on SiO2/indium tin oxide-coated glass substrates; Selective molecular assembly patterning at the nanoscale: a novel platform for producing protein patterns by elect, Nanotechnology, IOP, Bristol, GB, 16(9): 1781-1786 (2005).
Swinerd et al, Silk inverse opals from template-directed b-sheet transformation of regenerated silk fibroin, Soft Matter, 3(1 1):1377-1380 (2007).
Matsuno, K., The treatment of hydrofluoric acid burns, Occup. Med., 48(4):313-317 (1996).
No Author Listed, Impurities: Guideline for Residual Solvents Q3C (R5), ICH Harmonised Tripartite Guideline, International Conference on Harmonisation of Technical Requirements for Registration of Pharmaceuticals for Human Use, 29 pages (2011).

* cited by examiner

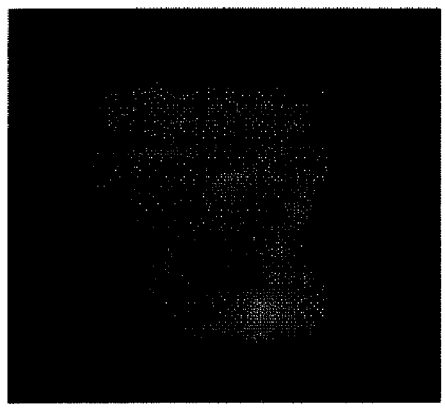
FIG. 6B
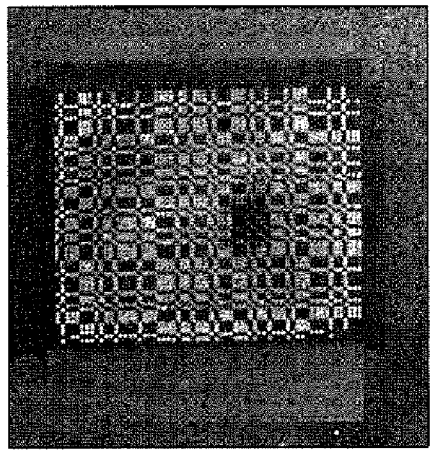
FIG. 6D
FIG. 6A
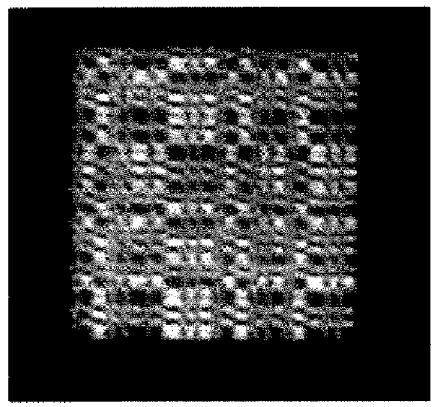
FIG. 6C

US 9,599,891 B2

FABRICATION OF SILK FIBROIN PHOTONIC STRUCTURES BY NANOCONTACT IMPRINTING

CROSS REFERENCE TO RELATED APPLICATIONS

This application is a 35 U.S.C. §371 National Phase Entry Application of International Application No. PCT/US2008/082487 filed Nov. 5, 2008, which designates the U.S., and which claims the benefit of priority under 35 U.S.C. §119(e) of U.S. Provisional application Ser. No. 60/985,310, filed on Nov. 5, 2007, which is hereby incorporated by reference in its entirety.

GOVERNMENT SUPPORT

The invention was made with government support under grant number FA95500410363, awarded by the Air Force Office of Scientific Research and contract number W911NF-07-1-0618, awarded by the U.S. Army Research Office. The government has certain rights in this invention.

FIELD OF THE INVENTION

The present invention is directed to biopolymer photonic structures, such as films and crystals, and methods for manufacturing such photonic crystals using nanocontact imprinting (nanoimprinting).

BACKGROUND OF THE INVENTION

The field of optics is well established. Some subfields of optics include diffractive optics, micro-optics, photonics, and guided wave optics. Various optical devices have been fabricated in these and other subfields of optics for research and commercial applications. For example, common optical devices include diffraction gratings, photonic crystals, optofluidic devices, waveguides, and the like.

Existing photonic films, crystals and other optical devices used are based on fabrication from glass, metallic, semiconductor, and elastomeric substrates. The choice of materials may be made based upon the application and the optical characteristics desired. These devices function well for traditional optical device needs, but generally involve significant use of non-biodegradable materials and remain in the environment for extended periods of time after the optical devices are removed from service and discarded. Additionally, these conventional materials suffer from poor biocompatibility during processing and function, as well as lack of degradability. Further, conventional labeling techniques that employ chemical dyes or labels such as quantum dots or functionalized metallic nanoparticles introduce external agents within the biological matrix potentially perturbing the interrogated biological functions.

Therefore, there exists an need for photonic structures such as photonic films and crystals based on biopolymers that are biodegradable, biocompatible, and minimize the negative impact to the environment. In addition, there exists a need for photonic structures that may provide additional functional features that are not provided by conventional photonic structures.

SUMMARY OF THE INVENTION

An object of the present invention provides for the processing of a biopolymer into photonic structures using nanoimprinting. Biopolymer-based nanoimprinted photonic structures, or "Biophotonic structures," and methods for manufacturing such photonic structures, move the frontier of nanodevices toward "living" or biological components and marry the precise options derived from biological molecular recognitions (e.g., enzymes, cells) with traditional photonics devices to address the material requirements. For example, problems with poor biodegradation of conventional biosensing devices may be solved by biodegradable photonic structures.

Additionally, the nanoimprinting processes of the present invention provide for a new class of active biophotonic nanodevices that open new opportunities for bio-sensing and bio-applications where spectral information can be customized in an organic, biocompatible structure without the need of fluorescent tags or chemical indicators.

The present invention provides for silk fibroin as the primary protein-based films for the realization of entirely organic biophotonic nano-materials and devices. Appropriate nanoscale geometries define light scattering regimes within the protein films that, in turn, lead to specifically engineered resonance phenomena ranging from traditional photonic crystal scattering (Braga scattering) to enhanced opalescence from nano textured, sub-wavelength biophotonic structures. By controlling the geometry of the nanopatterns, the present invention enables the design of custom spectral responses and controls the flow of light through biological samples.

In one embodiment of the present invention, silk is substituted for dielectrics or metallo-dielectrices to afford fabrication of biophotonic films, crystals, and other biophotonic structures. In accordance with one aspect of the present invention, a method of manufacturing a biocompatible nanopatterned biophotonic structure is provided. In one embodiment, the method includes providing a nano-imprinted substrate prepared using E-beam lithography, depositing a biopolymer matrix solution on the substrate, and drying the biopolymer matrix solution to form a solidified biopolymer film. A surface of the film is formed with a customized nanopattern mask on a surface of the film using E-beam lithograpy on the substrate, such that the biopolymer film exhibits a spectral signature corresponding to the E-beam lithograpy nanopattern formed on the surface of the substrate. The biophotonic structure may be a photonic film, a photonic crystal, a biophotonic structure, or the like. The substrate may be deposited by casting the substrate solution or by spin-coating the substrate solution.

The method of manufacturing the nanopatterned biophotonic structure may include forming the nanopattern using E-beam lithograpy nanoimprinting. Additionally, the nanopattern may be machined directly on a surface of the biopolymer film using E-beam lithography nanoimprinting techniques. Further, the nanopattern mask may be formed based on periodic photonic latices and non-periodic photonic lattices or a combination of lattices.

A nanopatterned biophotonic structure in accordance with an embodiment of the present invention may be biodegradable and may display optical activity in the form of opalescence. The biophotonic structure may be a nano-textured sub-wavelength biophotonic structure.

In accordance with one embodiment of the invention, the nanopatterned biopolymer films comprise silk, chitosan, collagen, gelatin, agarose, chitin, polyhydroxyalkanoates, pullan, starch (amylose amylopectin), cellulose, hyaluronic acid, and related biopolymers. In another embodiment, the method also includes embedding an organic material in the nanopatterned biopolymer film. For example, the organic material may be embedded in the nanopatterned biopolymer films and/or may be coated on a surface of the nanopatterned biopolymer films. Other materials may be embedded in the biopolymer or used in the coating, including biological materials or other materials depending upon the type of biopolymer photonic crystal desired. The devices may be processed within the biopolymer film, coupled to the surface of the device, or sandwiched within layers to further provide recognition and response functions. The organic material may be red blood cells, horseradish peroxidase, phenolsulfonphthalein, nucleic acid, a dye, a cell, an antibody, enzymes, for example, peroxidase, lipase, amylose, organophosphate dehydrogenase, ligases, restriction endonucleases, ribonucleases, DNA polymerases, glucose oxidase, laccase, cells, viruses, proteins, peptides, small molecules (e.g., drugs, dyes, amino acids, vitamins, antioxidants), DNA, RNA, RNAi, lipids, nucleotides, aptamers, carbohydrates, chromophores, light emitting organic compounds such as luciferin, carotenes and light emitting inorganic compounds (such as chemical dyes), antibiotics, antifungals, antivirals, light harvesting compounds such as chlorophyll, bacteriorhodopsin, protorhodopsin, and porphyrins and related electronically active compounds, or a combination thereof can be added.

Moreover, the substrate may include a nanopatterned surface so that when the biopolymer matrix solution is deposited on the nanopatterned surface of the substrate, the solidified biopolymer film is formed with a surface having a nanopattern thereon. In this regard, the substrate may be an optical device such as a bio-sensor, a lens, a microlens array, an optical grating, a pattern generator, a beam reshaper, or other suitable arrangement of geometrical features such as holes, pits, and the like. In one method in accordance with the present invention, the biopolymer matrix solution is an aqueous silk fibroin solution having approximately 1.0 wt % to 30 wt % silk, inclusive.

In another embodiment of the present invention, a nanopatterned biopolymer film is provided by machining a nanopattern on the solidified biopolymer film, for example, machining an array of holes and/or pits using E-beam lithography.

These and other advantages and features of the present invention will become more apparent from the following detailed description of the preferred embodiments of the present invention when viewed in conjunction with the accompanying drawings.

BRIEF DESCRIPTION OF THE DRAWINGS

FIG. 6(a) illustrates a scanning electron microscope picture of periodic silk nano-textured biophotonic structures.

FIG. 6(b) depicts an optical microscope picture showing the reflection of light from the periodic silk nano-textured biophotonic structure surface.

FIG. 6(c) shows an optical microscope picture showing the opalescence of non-periodic R-S silk nano-textured biophotonic structures.

FIG. 6(d) shows a scanning electron microscope picture of the non-periodic R-S silk.

DETAILED DESCRIPTION OF THE INVENTION

Figure 1A:
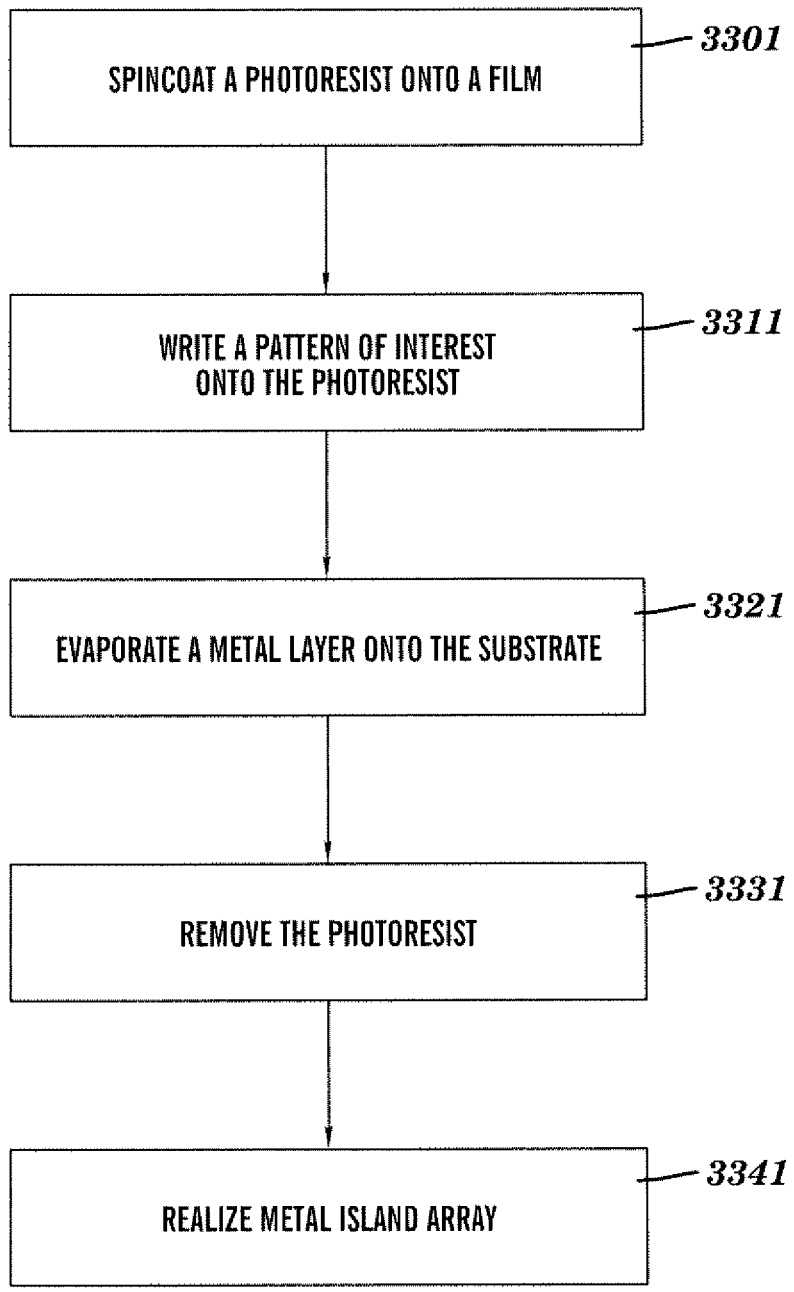
FIG. 1A illustrates is a flow diagram depicting a method for fabricating nano-textured biophotonic structures employing E-beam lithography for the nanoscale definition of two-dimensional patterns in accordance with the present invention.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference unless the context clearly indicates otherwise. Thus, for example, the reference to an excipient is a reference to one or more such excipients, including equivalents thereof known to those skilled in the art. Other than in the operating examples, or where otherwise indicated, all numbers expressing quantities of ingredients or reaction conditions used herein should be understood as modified in all instances by the term "about."

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

Unless defined otherwise, all technical and scientific terms used herein have the same meaning as those commonly understood to one of ordinary skill in the art to which this invention pertains.

The present invention provides for the engineering of light transport and control in biological matter, integration of photonic film and crystal optics, top-down nanofabrication techniques, and bio-compatible organic materials. In contrast to traditional photonic structures based on inorganic materials, biological matter presents a particular challenge because of a low refractive index. Nevertheless, the nanopatterning of photonic lattices on transparent biological templates provides a novel approach to mimic the naturally occurring opalescence phenomena encountered in the natural world, including butterfly wings iridescence due to the air/chitin nanostructure, despite the low refractive index of biopolymers.

Initially, note that biopolymer photonic crystals of the present invention are described herein below as being implemented with silk, which is biocompatible and biodegradable and exhibits superior functional characteristics and processability. In this regard, particular example embodiments comprise silkworm silk. There are many different silks, however, including spider silk, transgenic silks, recombinant silks, genetically engineered chimeric silks, and variants and combinations thereof, which are well known in the art and may be used to manufacture a biopolymer photonic structure as provided in the present invention.

Silk-based materials achieve their impressive mechanical properties with natural physical crosslinks of thermodynamically stable protein secondary structures also known as beta sheets (β-sheets). Thus, no exogenous crosslinking reactions or post process crosslinking is required to stabilize the materials. The presence of diverse amino acid side chain chemistries on silk protein chains facilitates coupling chemistry for functionalizing silks, such as with cytokines, morphogens, and cell binding domains. There are no known synthetic or biologically-derived polymer systems that offer this range of material properties or biological interfaces, when considering mechanical profiles, aqueous processing, room-temperature processing, ease of functionalization, diverse modes of processing, self-forming crosslinks, biocompatibility, and biodegradability.

Although no other biopolymer or synthetic polymer matches the range of features known of silk, some other polymers that exhibit various properties similar or analogous to silk have been identified by the present inventors. In particular, other natural biopolymers including chitosan, collagen, gelatin, agarose, chitin, polyhydroxyalkanoates, pullan, starch (amylose amylopectin), cellulose, hyaluronic acid, and related biopolymers have been identified. In view of the above noted features of biopolymers and of silk in particular, the present invention provides novel photonic structures, and methods for manufacturing such photonic crystals made from a biopolymer.

For example, some biopolymers, such as chitosan, exhibit desirable mechanical properties, can be processed in water, and forms generally clear films for optical applications. Some of these polymers are not easily processable in water. Nonetheless, such polymers may be used by themselves, or in combinations with silk, and may be used to manufacture biopolymer photonic structures for specific applications.

Photonic crystals (PCs) are periodic optical structures that are designed to control the dispersion and propagation of optical waves within a desired wavelength range. Photonic crystals may be periodic dielectric or metallo-dielectric structures that define allowed and forbidden electronic energy bands. In this fashion, photonic crystals are designed to affect the propagation of electromagnetic (EM) waves in the same manner in which the periodic potential in a semiconductor crystal affects electron motion.

Photonic crystals include periodically repeating internal regions of high and low dielectric constants. Photons propagate through the structure based upon the wavelength of the photons. Photons with wavelengths of light that are allowed to propagate through the structure are called "modes." Photons with wavelengths of light that are not allowed to propagate are called "photonic band gaps." The structure of the photonic crystals defines allowed and forbidden electronic energy bands. The photonic band gap is characterized by the absence of propagating EM modes inside the structures in a range of wavelengths and may be either a full photonic band gap or a partial photonic band gap, and gives rise to distinct optical phenomena such as inhibition or enhancement of spontaneous emission, spectral selectivity of light, or spatial selectivity of light.

Engineered photonic crystals are artificial dielectrics in which the refractive index is modulated over length scales comparable to the wavelength of light. These structures behave as semiconductor crystals for light waves. Indeed, in periodic structures the interference is constructive in well-defined propagation directions, which leads to Bragg scattering and light refraction. At high enough refractive index contrast, light propagation is prohibited in any direction within a characteristic range of frequencies. As described above, this phenomenon is referred to as a photonic band gap, in analogy with the electronic band gap in a semiconductor. Because the basic physics of photonic crystals relies on Bragg scattering, the periodicity of the crystal lattices has to be commensurate with the wavelength of light. The specific choice of the building-block materials (i.e., the refractive index contrast) and lattice type (lattice symmetries, spatial frequencies) plays a crucial role in determining the spectral selectivity and light-transport/scattering properties of photonic crystals devices.

In fact, the refractive index contrast (the relative difference in refractive index of the core transport medium and the cladding medium), is a key parameter for the emergence of strong photonic crystals phenomena such as bright opalescence, coherent multiple scattering, light localization, and ultimately the formation of complete photonic band gaps. Strong photonic crystal effects at low refractive index contrast occur frequently in nature, for example, the iridescence of an opal gemstone or the color of a butterfly wing. This effect is at the basis of "structural colors", which are colors that originate purely from materials organization and structure, as opposed to intrinsic properties such as pigments and impurities.

Such photonic crystal device structures can be used for high-reflecting omni-directional mirrors and low-loss waveguides. Photonic crystals are attractive optical devices for controlling and manipulating the flow of light. Photonic crystals are also of interest for fundamental and applied research and are being developed for commercial applications. Two-dimensional periodic photonic crystals are being used to develop integrated-device applications.

Strong photonic crystals effects at low refractive index contrast occur frequently in nature, including the iridescence of an opal gemstone or the color of a butterfly wing. For example, the Morpho butterfly (*Morpho menelaus*) wing iridescence is due to the air/biopolymer (n~1.5) nanostructure. See, e.g., Vukusic et al., 266 Proc. Roy. Soc. Lond. B 1403-11. (1999). When acetone (n=1.36) is dropped on the wing, the iridescence color changes from blue to green because of the decreased index contrast in the photonic lattice, now filled with acetone instead of air. These effects are at the basis of 'structural colors,' which are colors that originate purely from materials organization and structure, as opposed to intrinsic properties such as pigments and impurities.

Lithographic techniques facilitate development of nanoscale devices by selectively removing portions of thin films or substrates. Electron beam lithography ("E-beam lithography") is a surface preparation technique that scans a beam of electrons in a patterned fashion across a film-covered surface, called a "resist." E-beam lithography selectively removes either exposed or non-exposed regions of the resist as its "developing" technique. E-beam lithography may be used to create very small structures in the resist that can subsequently be transferred into another material for a number of purposes, such as to create very small electronic devices. An advantage of E-beam lithography is that it may be used to exceed the diffraction limit of light and to make structural features in the nanometer range.

The E-beam nanoimprinting of the present invention provides for complete photonic band gaps that can be achieved at a lower refractive index contrast (compared to inorganic dielectrics like silicon, for example) by using non-periodic photonic structures such as quasi-crystals, fractals and optical amorphous structures, which possess long-range order (and different degrees of short-range order) without translational invariance.

Using methods in accordance with the present invention, it is possible to directly nano-pattern biological matter to open new avenues of "reagent-less" detection, where the optical signature is generated by designed nano-patterns (nano-texturing) as opposed to the addition of external indicators. To achieve this goal, silk fibroin is used as the basis for the photonic crystal structures to take advantage of the strongest and toughest natural polymeric material known. Furthermore, the versatile chemistry due to the amino acid side chain chemistries (when compared to polydimethylsiloxane (PDMS), for example), controlled processability in all aqueous systems at ambient conditions, and controllable lifetimes due to enzymatic degradability, provide a versatile template upon which to build such a technological advance. Finally, the optical transparency and the material robustness of silk films is suited for the development of the optical platforms. Further extension of the nano-patterned biophotonic crystals can be obtained by embedding functional biological components within the silk fibroin films.

Tuning the colorimetric response as a function of the entrained biological activity radically impacts the areas of biomaterials processing, measurement, control, and sensing. The availability of a biological matrix that has the material toughness to withstand room temperature use in an uncontrolled environment while simultaneously exhibiting high optical quality and biological activity is unique. The present invention enables miniaturization and integrated biological spectral analysis in a convenient environment by directly embedding a chosen analyte in a "biopolymer nanophotonic assay," or "nano-textured biophotonic structure." Sophisticated optical interfaces that couple light into and out of the bulk devices such as lens arrays, beam reshapers, pattern generators, 1-D or 2-D gratings, and the like, may be realized in a compact package. In addition, the ability to prepare, process, and optimize this platform system in all aqueous environments at ambient conditions broadens versatility by allowing the direct incorporation and stabilization of labile biological "receptors" in the form of peptides, enzymes, cells, or related systems.

Figure 4:
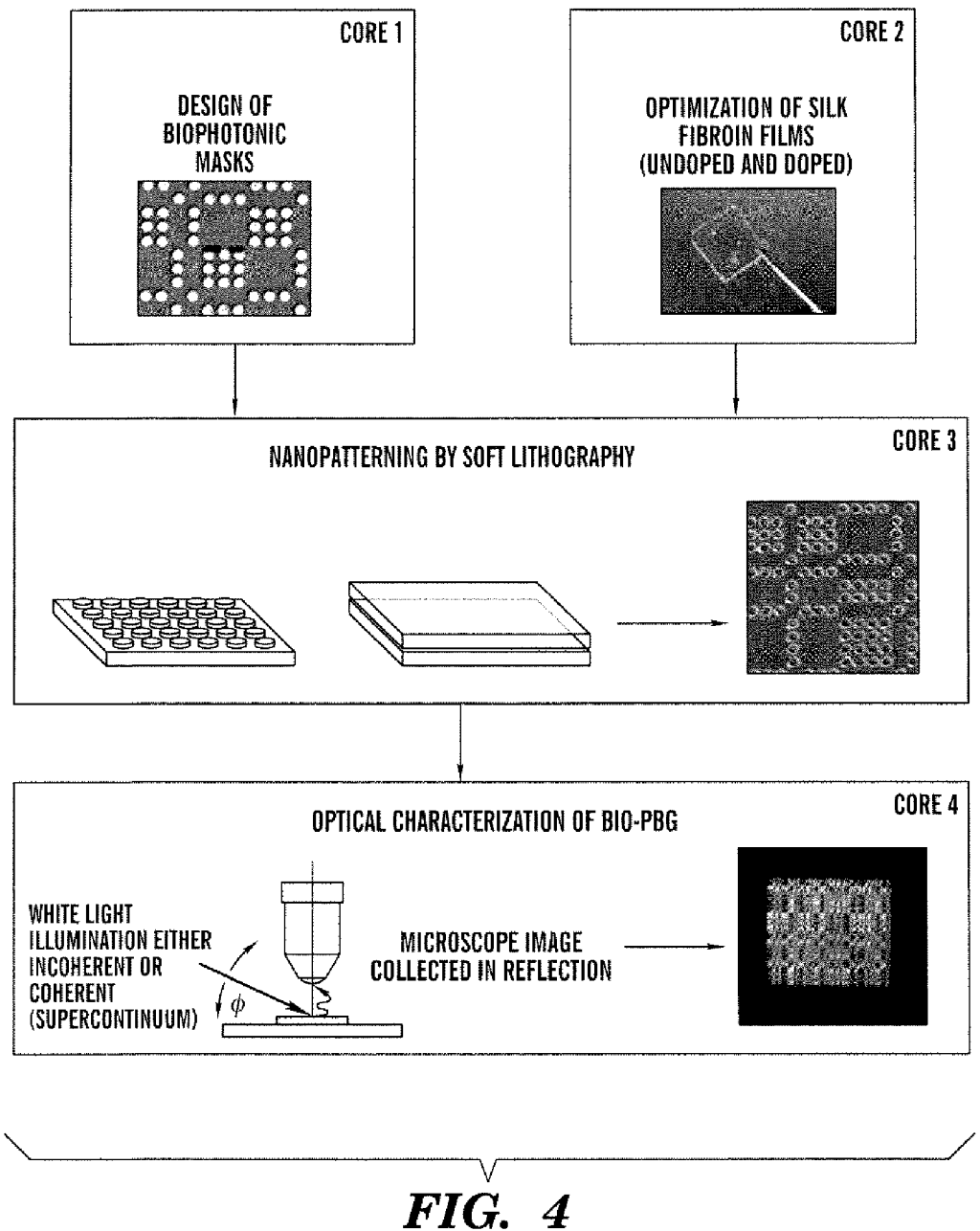
FIG. 4 depicts a system overview of the fabrication process of nano-textured biophotonic structures in accordance with the present invention.
Figure 5B:
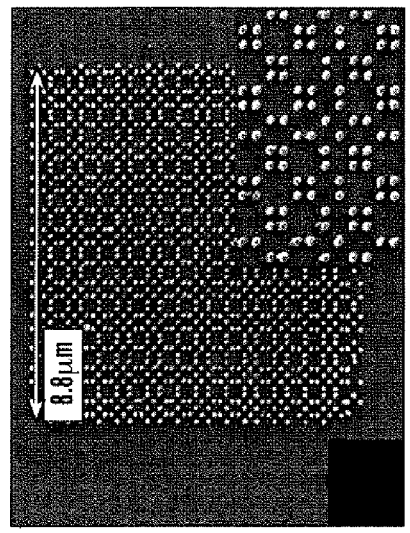
FIGS. 5(a)-5(d) show E-beam fabricated masks for nano-imprinting on silk fibroins.
Figure 5D:
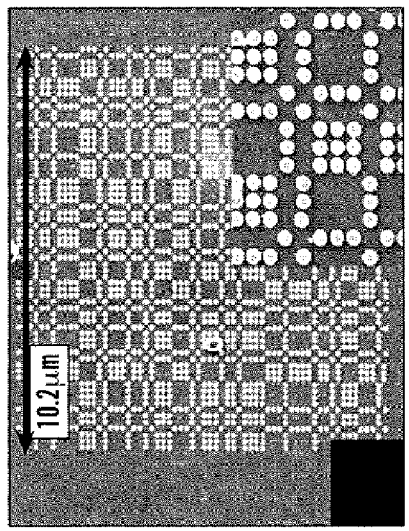
Figure 5A:
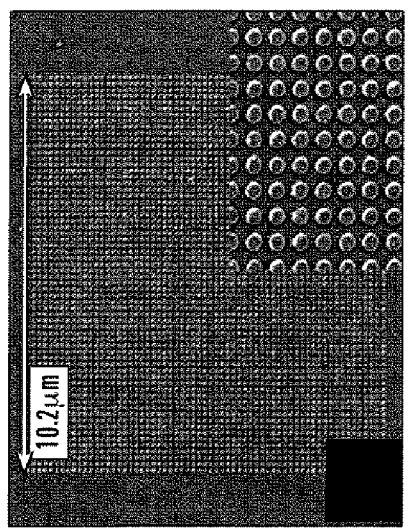
Figure 5C:
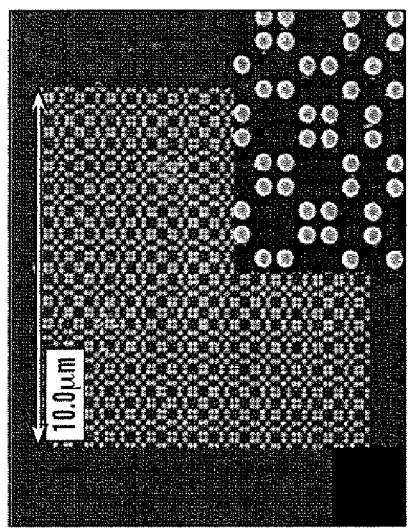

As illustrated in FIG. 4, core areas of focus include the design of biophotonic masks and the optimization of silk fibroin films. An aperiodic structure, such as Cr on Si mask, with individual features having 250 nm in diameter used as a template for nano-imprinting. The substrate may be optimized for transparency, low impurity, and flatness. The resulting patterned structure in silk was obtained using the Cr/Si template and soft lithography. The silk-nano-textured biophotonic structure is characterized for their optical response. The results shown herein demonstrate the spectral selectivity of the imprinted silk under white light illumination. The silk fibroin film includes a 1 cm×1 cm silk substrate that contains the nanostructures.

The term "nanopatterned" as used herein refers to very small patterning that is provided on a surface of the biopolymer films, the patterning having structural features of a size that can be appropriately measured on a nanometer scale. For example, sizes ranging from 100 nm to a few microns are typical of the patterning used in accordance with the present invention.

Figure 2:
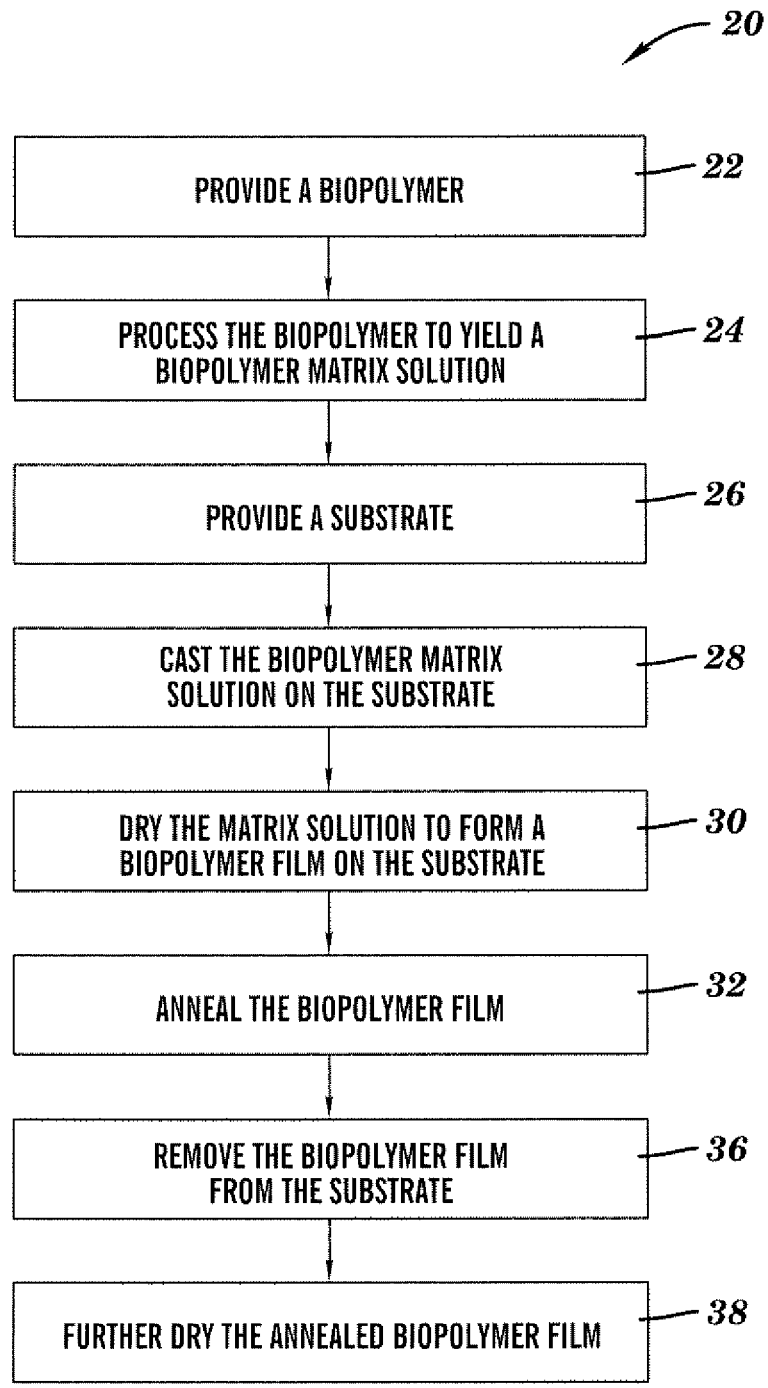
FIG. 2 is a schematic flow diagram illustrating a method for manufacturing a biopolymer film or films used to fabricate the biocompatible biopolymer photonic structure in accordance with one embodiment.

FIG. 2 is a schematic flow diagram 20 illustrating one method for manufacturing nanopatterned biopolymer films for use in manufacturing a biopolymer photonic structure in accordance with one embodiment of the present invention. In particular, a biopolymer is provided in step 22. In the example where the biopolymer is silk, the silk biopolymer may be provided by extracting sericin from the cocoons of *Bombyx mori*. The provided biopolymer is processed to yield a biopolymer matrix solution in step 24. In one embodiment, the biopolymer matrix solution is an aqueous solution. In other embodiments, solvents other than water or a combination of solvents may be used, depending on the biopolymer provided.

Thus, in the example of silk, an aqueous silk fibroin solution is processed in step 24, for example, 8.0 wt %, which is an example of the concentration used to manufacture the biopolymer films of one embodiment of the biopolymer photonic crystal. Alternatively, in other embodiments, the solution concentrations may also be varied from very dilute (approximately 1 wt %) to very high (up to 30 wt %) using either dilution or concentration, for example, via osmotic stress or drying techniques. Production of aqueous silk fibroin solution is described in detail in WO 2005/012606, entitled "Concentrated Aqueous Silk Fibroin Solution and Uses Thereof."

A substrate is provided in step 26 to serve as a mold in manufacturing the biopolymer film. The aqueous biopolymer matrix solution is then cast on the substrate in step 28. The biopolymer matrix solution is dried in step 30 to transition the aqueous biopolymer matrix solution to the solid phase. In this regard, the aqueous biopolymer matrix solution may be dried for a period of time such as 24 hours, and may optionally be subjected to low heat to expedite drying of the aqueous biopolymer solution. Other drying techniques may also be used such as isothermal drying, roller drying, spray drying, and heating techniques. Upon drying, a biopolymer film is formed on the surface of the substrate. The thickness of the biopolymer film depends upon the volume of the biopolymer matrix solution applied to the substrate.

Figure 8:
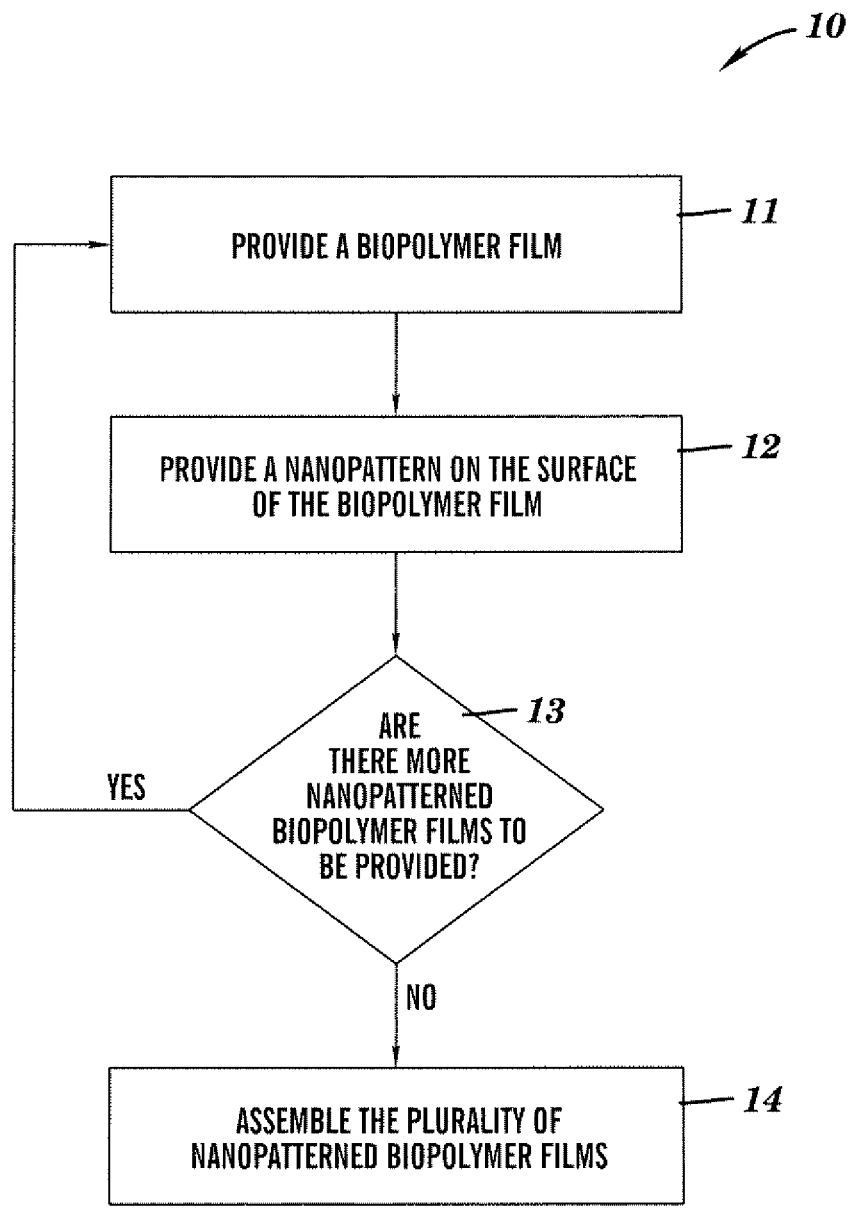
FIG. 8 is a schematic flow diagram illustrating a method for manufacturing a biocompatible biopolymer photonic crystal in accordance with one embodiment of the present invention.

Once the drying is complete and the solvent of the biopolymer matrix solution has evaporated, the biopolymer film may be optionally annealed in step 32. This annealing step may be performed within a water vapor environment, such as in a chamber filled with water vapor, for different periods of time depending on the material properties desired. Typical time periods may range from two hours to two days, for example, and the optional annealing may also be performed in a vacuum environment. The annealed biopolymer film is then removed from the substrate in step 34 and allowed to dry further in step 36. The film manufactured in the above-described manner can be used as a photonic crystal that is biocompatible and biodegradable. Alternatively, annealing may be accomplished by contacting the film with a methanol or ethanol solution. In addition, a plurality of such films can be used in manufacturing a biopolymer photonic crystal in accordance with the method of FIG. 8.

In one embodiment, the surface of the substrate has the appropriate nanopattern thereon, as provided by E-beam nano lithography, so that when the solidified biopolymer film is removed from the substrate, the biopolymer film is already formed with the desired nanopattern on a surface thereof. In such an implementation, the substrate may be an optical device such as a nanopatterned optical grating, depending on the nanopattern desired on the biopolymer films. The ability of the biopolymer casting method using a nanopatterned substrate for forming highly defined nanopatterned structures in the resultant biopolymer films was verified, and silk films having nanostructures as small as 75 nm and RMS surface roughness of less than 5 nm have been demonstrated.

The measured roughness of cast silk film on an optically flat surface shows measured root mean squared roughness values between 2.5 nm and 5 nm, which implies a surface roughness easily less than $\lambda/50$ at a wavelength of 633 nm. Atomic force microscope images of patterned silk diffractive optics show the levels of microfabrication obtainable by casting and lifting silk films off of appropriate molds. The images show definition in the hundreds of nanometer range and the sharpness of the corners indicates the possibility of faithful patterning down to the tens of nanometers.

The film properties, such as thickness and biopolymer content, as well as optical features, may be altered based on the concentration of fibroin used in the process, the volume of the aqueous silk fibroin solution deposited, and the post deposition process for drying the cast solution. Accurate control of these parameters is desirable to ensure the optical quality of the resultant biopolymer optical device and to maintain various characteristics of the biopolymer optical device, such as transparency, structural rigidity, or flexibility. Furthermore, additives to the biopolymer matrix solution may be used to alter features of the biopolymer optical device such as morphology, stability, and the like, as with glycerol, polyethylene glycols, collagens, and the like.

The structural stability and ability to have a nanostructure thereon makes the above-described silk films appropriate for use as a biophotonic structure and for use in manufacture of biopolymer photonic crystals. As noted previously, the material properties of silk films are well-suited for patterning on the nanoscale, for example, using soft lithography and E-beam machining techniques. With appropriate relief masks, silk films may be cast and left to solidify upon the surface and subsequently detached. The silk casting and solidification process allows the formation of highly-defined patterned structures on the nanoscale as described below which enables the production of biopolymer films that can be used for manufacturing biopolymer photonic crystals.

Important advantages and functionality can be attained by the biopolymer photonic crystal in accordance with the present invention, whether it is implemented by a single film or by an assembly of stacked films. In particular, the biopolymer photonic structure can be biologically functionalized by optionally embedding it with one or more organic indicators, living cells, organisms, markers, proteins, and the like. More specifically, the biopolymer photonic structures in accordance with the present invention may be embedded or coated with organic materials such as red blood cells, horseradish peroxidase, phenolsulfonphthalein, nucleic acid, a dye, a cell, an antibody, enzymes, for example, peroxidase, lipase, amylose, organophosphate dehydrogenase, ligases, restriction endonucleases, ribonucleases, DNA polymerases, glucose oxidase, laccase, cells, viruses, proteins, peptides, small molecules (e.g., drugs, dyes, amino acids, vitamins, antioxidants), DNA, RNA, RNAi, lipids, nucleotides, aptamers, carbohydrates, chromophores, light emitting organic compounds such as luciferin, carotenes and light emitting inorganic compounds (such as chemical dyes), antibiotics, antifungals, antivirals, light harvesting compounds such as chlorophyll, bacteriorhodopsin, protorhodopsin, and porphyrins and related electronically active compounds, tissues or other living materials, other compounds or combinations thereof. The embedded organic materials are biologically active, thereby adding biological functionality to the resultant biopolymer photonic structure.

The embedding of the biopolymer photonic structure with organic materials may be performed for example, by adding such materials to the biopolymer matrix solution used to manufacture the biopolymer films, such as the silk fibroin matrix solution. In an implementation where the biopolymer photonic crystal is manufactured by stacking a plurality of biopolymer films, the photonic crystal can be biologically functionalized by functionalizing of one or more of the biopolymer films. Alternatively, or in addition thereto, such added organic materials can be sandwiched between the biopolymer film layers that make up the biopolymer photonic crystal in such an implementation.

The biologically induced variation in the photonic bandgap and spectral selectivity of the resultant biopolymer photonic crystal can be used to determine the presence of particular substances, and biological processes can also be sensitively monitored optically. In particular, such substances may be detected based on the changes in the optical properties of the biopolymer photonic crystal, since the change in spectral selectivity can be correlated to the features of the photonic crystal structure and/or to the organic materials embedded therein. This is especially advantageous in applications where biopolymer photonic crystals are used as sensors to provide recognition and/or response functions.

Correspondingly, as explained, dielectrics and metallo-dielectrics used in conventional photonic crystals can be replaced with silk or with other biopolymers in accordance with the present invention to allow the fabrication of biopolymer photonic crystals. In addition, the present invention may be used to provide customized biopolymer photonic crystals for use as bio-optical filters by allowing the variability of the bandgap or tuning of the biological-bandgaps.

Furthermore, it should also be appreciated that further fabrication of biophotonic bandgap materials and functionalization may be performed by hybridizing the biopolymer photonic crystal of the present invention. For example, the biopolymer photonic crystal and/or biopolymer films constituting the photonic crystal may be deposited with thin metallic layers to provide differing optical characteristics. The bulk index of the biopolymer photonic crystal can be affected in this manner to enhance the contrast factor and to tailor the spectral selectivity. Such hybridized biopolymer photonic crystals may be advantageously used as bioplasmonic sensors, thereby integrating electromagnetic resonance, optics, and biological technologies together in a biocompatible optical device.

NBS and Bio-Photonic Crystals: Nanofabrication and Design

The integration of photonic crystal optics, top-down nanofabrication techniques, and bio-compatible organic materials offers the ultimate potential for the engineering of light transport and control on biological matter. In contrast to traditional photonic crystal structures based on inorganic materials, biological matter presents a particular challenge because of a low refractive index. Nevertheless, the nano-patterning of photonic lattices on transparent biological templates constitutes a novel approach to mimic the naturally occurring opalescence phenomena encountered in the natural world (e.g., butterfly wings), despite the low refractive index of biopolymers.

Figure 1B:
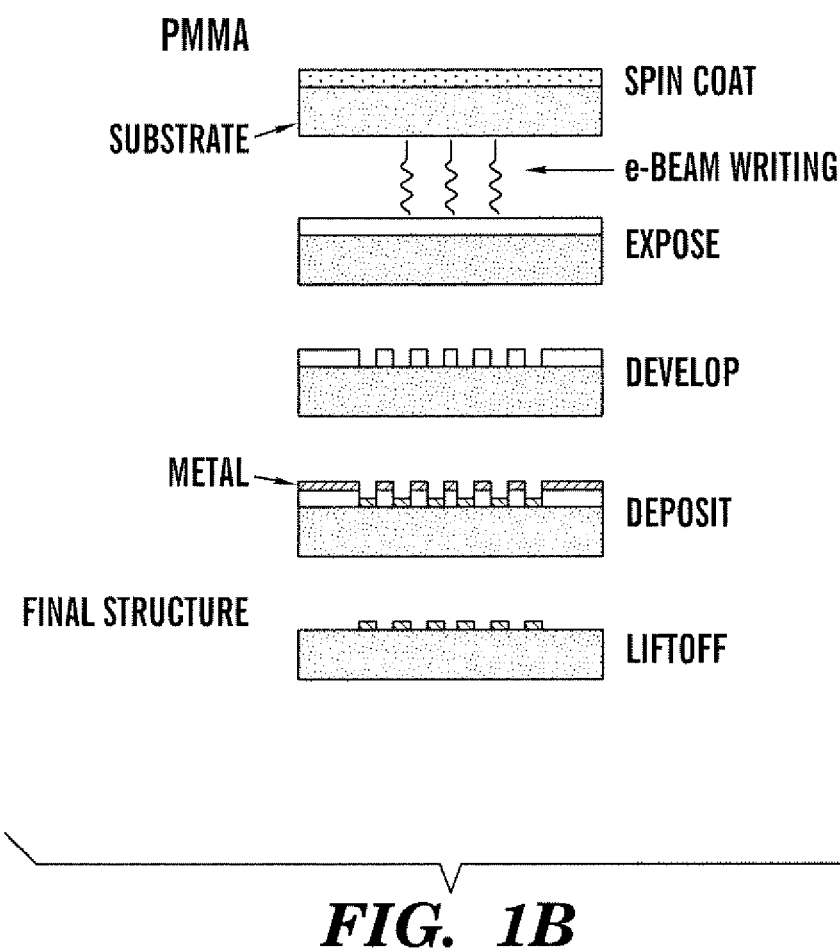
FIG. 1B shows a schematic representation of a photoresist patterned using E-beam lithography in accordance with the present invention.

As shown in FIGS. 1A and 1B, the system and method of the present invention for fabricating NBS employs E-beam lithography performed on Si wafers for the nanoscale definition of two-dimensional patterns, which are transferred to transparent silk fibroins via a soft nano-imprint process. FIG. 1 illustrates an E-beam lithography system with which a nanopattern may be written onto a photo resist in accordance with the present invention and a graphical representation of a photoresist patterned using the method. The E-beam lithography produces periodic and aperiodic metal island arrays with desired geometries. The process is shown in FIG. 1A. In step 3303, a photoresist is spincoated onto a film. For example, in one embodiment of the present invention, a layer of 200 nm Poly(1-vinylpyrrolidone-co-2-dimethylamino-ethylmethaerylate) (PMMA) photoresist is spincoated on a 30 nm thick indium tin-oxide (ITO) film on quartz (or a Si wafer). Then, in step 3311, a pattern of interest is written onto the photoresist. For example, in one embodiment of the present invention, the pattern of interest will be written using a Jeol JSM-6400 SEM equipped with a Deben beam blanker. In step 3321, a metal layer is evaporated onto the substrate. For example, in one embodiment of the invention, after photoresist patterning, a 35 mm thick metal (for instance Cr, Au, Ag, Al) layer is evaporated onto the substrate. In step 3331, the photoresist is removed to realize a metal island array. In one embodiment of the present invention, the photoresist is removed in Acetone, exposing the metal island array on indium-tin-oxide (ITO).

Figure 3:
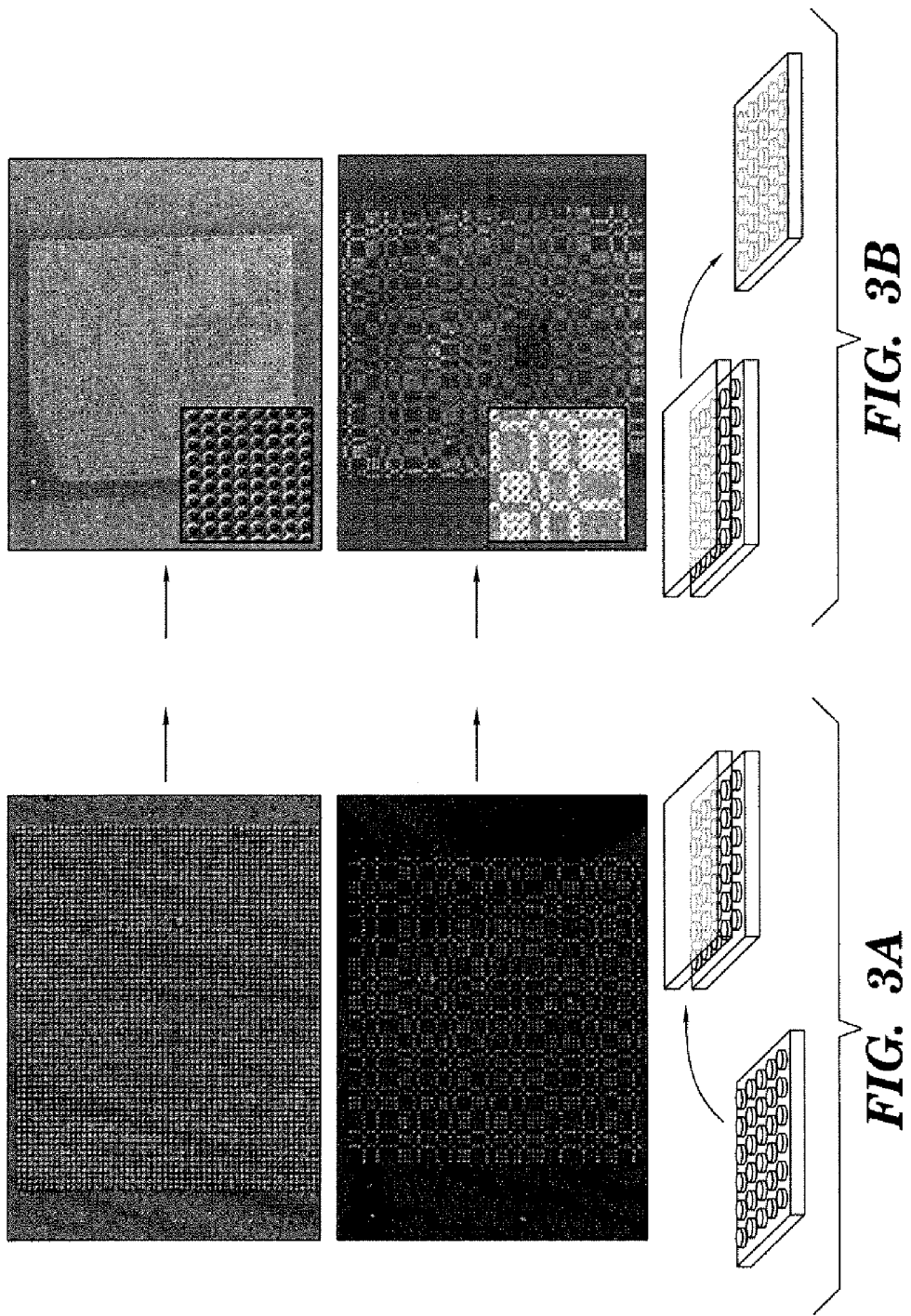
FIGS. 3A and 3B illustrate E-beam fabricated masks for nano-imprint on silk fibroins.

In one embodiment of the present invention, an NBS was fabricated on transparent silks by using a Cr/Si hard mask as shown in FIGS. 3 and 4. FIG. 4 shows E-beam fabricated masks for nano-imprint on silk fibroins. The masks in (a) and (c) include 100 nm diameter (50 nm height) Cr nanoparticles with 50 nm spacing on a Si substrate. The typical particle spacing illustrated in FIG. 5 varied from 50 nm to 500 nm, depending upon the writing conditions. The resulting nano-printed NBS on silk fibroins are shown in (b) and (d) of FIG. 5. Optical activity was demonstrated using the Cr/Si hard mask. The method of the present invention provides for label-free spectral signatures directly on biological matter, without the need to rely on fluorescent tags or chemical dyes.

This is particularly important in biological and biomedical imaging, where the design of structural colors in a biological substrate would offer an un-intrusive way to monitor the evolution of biological systems without using physical markers. In addition, NBS offers a novel and powerful approach to bio-optical sensing and imaging when combined with appropriately functionalized substrates.

The system and method of the present invention may be used to systematically determine the role of periodicity, deterministic disorder, and randomness for the control of structural colors in biological templates. In particular, the present inventors have fabricated NBS chips to customize pattern morphology (periodic versus non-periodic), pattern dimensionality, and specific mask materials in relation to the creation of photonic gaps and strong opalescence/scattering in NBS. Specifically, the method of the present invention may be used to to print arrays of sub-wavelength holes spaced from 50 nm to 500 nm. Accessing additional ranges of interspacing distances and particle dimensions enable the incorporation of different scattering regimes, from Rayleigh and Mie single scattering to multiple scattering and coherent Bragg scattering (periodic arrays). This approach can easily be extended to the fabrication of deterministic arrays based on the novel concept of aperiodic order. Deterministic Aperiodic Arrays are characterized by long-range order without translational invariance. Namely, they are non-periodic but deterministic (regular/ordered). As a result, their physical properties approach those of random and amorphous solids, displaying large photonic band-gaps and localized light states.

Additionally, dielectric, two-dimensional deterministic aperiodic structures may lead to the formation of complete photonic bandgaps at lower refractive index contrast with respect to their periodic counterparts. Further, a method of the present invention may include periodic lattices, Fibonacci quasi-periodic lattices, Thue-Morse (TM) aperiodic lattices, Rudin-Shapiro (RS) aperiodic lattices, random lattices, and other deterministic aperiodic lattices based on number theoretic sequences. The lattices in Fibonacci quasi-periodic lattices, Thue-Morse (TM) aperiodic lattices, and Rudin-Shapiro (RS) aperiodic lattices are chief examples of deterministic aperiodic lattices with increasing degrees of complexity. In particular, the Rudin-Shapiro lattice possesses a flat spectrum of spatial frequencies (white Fourier spectrum) and can be simply thought of as the analogue of a "photonic amorphous or a fluid structure." As further described below, light scattering from these "photonic fluids" may be dramatically enhanced leading to an analogy of crystal opalescence.

Enhanced Opalescence of Silk Fibroin NBS by Nanoimprint

Using a method in accordance with the present invention, silk biophotonic bandgap optical elements may be realized with a (modified) soft lithography approach. Casting silk on patterned diffractive optical surfaces such as holographic diffraction gratings with varying line pitches as masks resulted in optical features as small as 200 nm. Further, the same protocol used for the diffractive optics may be applied to the E-beam written masks. In one embodiment, the silk solution is cast on the mask and is allowed to dry for two hours. The silk is then removed from the mask by simple mechanical lifting of the grating from the substrate. Upon separation of the grating from the silk film, the resulting imprinted pattern is analyzed by scanning electron microscopy. The results are shown in FIG. 3 and in FIG. 6, which demonstrates the fidelity obtainable with this approach.

Figure 7A:
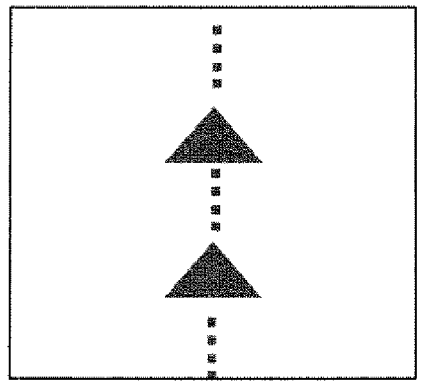
FIG. 7(a) shows a schematic diagram of a mask design with nanopatterns alternating between alignment arrows.
Figure 7B:
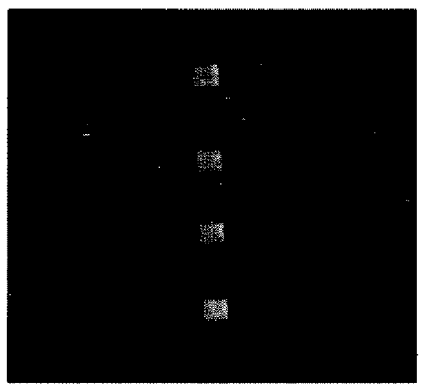
FIG. 7(b) shows experimentally measured reflection patterns from Thue-Morse BNS.
Figure 7C:
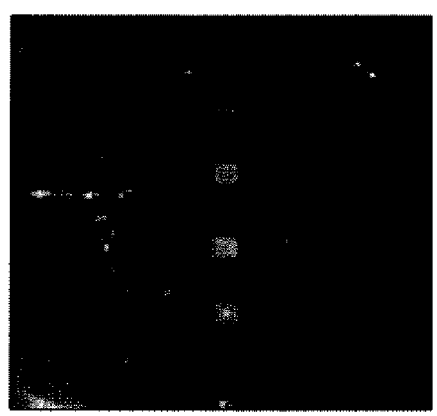
FIG. 7(c) shows experimentally measured reflection patterns from various sized BNS.

Using these nano-patterning capabilities, optical characterization of these structures may be performed to customize the spectral response induced by the nano-patterns. In accordance with the present invention, films may be examined by shining a white light incoherent source and collecting the reflected image from the surface with a microscope. The results are shown in FIG. 3, FIG. 5, and FIG. 6. The imprinted areas on the films strongly scatter light and appear colored under white light illumination. Under higher magnification, the spectral distribution of the impinging white light follows the etched patterns as shown in FIG. 7(*c*), with different spectral bands selected in different areas of the imprinted surface. This bright opalescence phenomenon in NBS increases in its intensity as we move from periodic to deterministic non-periodic arrays. This result naturally suggests a link between the abundance of spatial frequencies (disorder) in aperiodic structures and the formation of multiple optical gaps. This fascinating phenomenon, as observed in R-S structures, may be regarded as the optical analogue of critical opalescence in a "photonic fluid." This is a consequence of the fact that the R-S system has no characteristic length and is therefore scale-invariant, exhibiting fluctuations and scattering at all length scales.

The nano-imprinting approach of the present invention may be further optimized by controlling important process variables such as silk solution concentration, cross-linking and annealing, master pattern substrates, and lift-off methods, in order to bring controllable optical functionality and maximum patterned areas to the biological matrix. Controlled nano-patterned film formation may be performed under different conditions by varying the environmental and mechanical parameters, including solvent, solution concentration, annealing times, surface orientation, and the like, to name a few. Similarly, post-processing of the crystallized films may also be varied to control the nano-patterned film formation. These parameters may be varied to maximize the optical quality (including flatness and transparency) of the generated films and to understand the fundamental relationships between processing and material functions derived from crystal size, distribution and orientation at both surfaces and bulk regions of the films.

Additional methods in accordance with the invention may be used to manipulate light by employing optical physics mediated by nanopatterned imprints on biological matter. Further, using phenomena such as light localization, however, a severe limitation of existing technology to realize optical bio-nanostructures is the lack of a universal substrate that can simultaneously possess excellent optical and mechanical properties, are thermodynamically stable, and have controllable chemical resistance, ease of integration with various substrates, and bio-compatibility. The proposed approach on biopolymer photonics aims to systematically tackle this long-standing problem. In particular, this research has the potential to significantly advance the state-of-the-art with respect to current bio-sensing technology. The controlled fabrication of an array of biologically active optical elements in silk would open an innovative area of optical assays that can relay orthogonal information about biological activity embedded in the optical element or, conversely, manipulate light through biological structure or biological function. With the successful implementation of these devices, radically new optical sensing approaches and light manipulation can be developed by operating at the interface between the biological and physical sciences.

The foregoing description of the aspects and embodiments of the present invention provides illustration and description, but is not intended to be exhaustive or to limit the invention to the precise form disclosed. Those of skill in the art will recognize certain modifications, permutations, additions, and combinations of those embodiments are possible in light of the above teachings or may be acquired from practice of the invention. Therefore, the present invention also covers various modifications and equivalent arrangements that fall within the purview of the appended claims.

What is claimed is:

1. A method of manufacturing a biophotonic nano-material, the method comprising steps of:
   providing a substrate having a lithographically nanopatterned structure on a surface thereof;
   providing an aqueous silk-fibroin solution;
   depositing the solution on the lithographically nanopatterned surface of the substrate;
   drying the solution to form a solidified silk-fibroin film having a surface in contact with the nanopatterned surface of the substrate, which film is characterized by beta-sheet secondary structure and by a nanopatterned imprint in the contacted surface of the film transferred from the nanopatterned surface of the substrate; and
   mechanically removing the film from the substrate,
   wherein the film is characterized in that when it is exposed to photonic radiation it exhibits it spectral response corresponding to the lithographically nanopatterned imprint, and
   wherein the biophotonic nano-material is characterized such that when a biological material selected from the group consisting of red blood cells, horseradish peroxidase, a nucleic acid, cells, an antibody, enzymes, peroxidase, lipase, amylose, organophosphate dehydrogenase, ligases, restriction endonuclease, ribonucleases, DNA polymerases, glucose oxidase, laccase, viruses, proteins, peptides, amino acids, DNA, RNA, RNAi, nucleotides, bacteriorhodopsin, and protorhodopsin is embedded in the film or coated on its surface, one or both of its structure and its biological activity is not materially degraded, reduced, and/or inhibited.

2. The method of claim 1, wherein prior to the step of providing the substrate, the method comprises:
   spin-coating a resist on the surface of the substrate;
   e-beam writing the nanopattern on the resist;
   developing the resist to selectively remove areas of it;
   evaporating a metal layer onto the surface of the substrate; and
   removing the resist to expose a metal island array, thereby forming the nanopatterned structure on the surface of the substrate.

3. The method of claim 1, wherein the biophotonic nano-material is biocompatible.

4. The method of claim 1, wherein the biophotonic nano-material is biodegradable.

5. The method of claim 1, wherein the nanopatterned structure comprises an array of at least one of holes and pits.

6. The method of claim 5, wherein the holes are spaced apart from 50 nm to 500 nm, inclusive.

7. The method of claim 5, when the nanopatterned structure comprises holes, the holes are spaced apart from 50 nm to 500 nm, inclusive.

8. The method of claim 1, wherein the nanopatterned structure is based on non-periodic photonic lattices.

9. The method of claim 1, wherein the spectral response exhibited is the form of an opalescent response.

10. The method of claim 1, wherein the step of providing an aqueous silk-fibroin solution comprises providing a solution in which is present at approximately 1 wt % to 30 wt % inclusive.

11. The method of claim 1, wherein the nanopatterned structure is a template for an optical device.

12. The method of claim 11, wherein the optical device is at least one of a lens, a microlens array, an optical grating, a pattern generator, and a beam reshaper.

13. The method of claim 11, wherein the optical device is an arrangement of geometrical features.

14. The method of claim 11, wherein the arrangement of geometrical features is holes and/or pits.

15. The method of claim 1, wherein the nanopatterned structure is a template for a biosensing device.

16. The method of claim 1, wherein the nanopatterned structure comprises 100 nm diameter Cr nanoparticles on a Si substrate.

17. The method of claim 16, wherein the Cr nanoparticles are spaced from 20 nm to 250 nm, inclusive.

18. The method of claim 1, further comprising a step of coating the biophotonic nano-material with one or more components selected from the group consisting of: red blood cells, horseradish peroxidase, a nucleic acid, cells, an antibody, enzymes, peroxidase, lipase, amylose, organophosphate dehydrogenase, ligases, restriction endonucleases, ribonucleases, DNA polymerases, glucose oxidase, laccase, viruses, proteins, peptides, amino acids, DNA, RNA, RNAi, nucleotides, bacteriorhodopsin, and protorhodopsin.

19. The method of claim 1, the step of providing the aqueous silk-fibroin solution, comprises adding to the aqueous silk-fibroin solution one or more components selected from the group consisting of: red blood cells, horseradish peroxidase, a nucleic acid, cells, an antibody, enzymes, peroxidase, lipase, amylose, organophosphate dehydrogenase, ligases, restriction endonucleases, ribonucleases, DNA polymerases, glucose oxidase, laccase, viruses, proteins, peptides, amino acids, DNA, RNA, RNAi, nucleotides, bacteriorhodopsin, and protorhodopsin and thereby embedding the biophotonic nano-material.

* * * * *